United States Patent [19]
Godfrey et al.

[11] 4,051,315
[45] Sept. 27, 1977

[54] 6"-DEOXYKANAMYCIN B AND 6"-DEOXYTOBRAMYCIN

[75] Inventors: John Carl Godfrey, Syracuse; Joseph Rubinfeld, Northport, both of N.Y.

[73] Assignee: Bristol-Myers Company, New York, N.Y.

[21] Appl. No.: 636,886

[22] Filed: Dec. 2, 1975

Related U.S. Application Data

[63] Continuation-in-part of Ser. No. 523,292, Nov. 13, 1974, abandoned.

[51] Int. Cl.$^2$ ............................................. C07H 15/22
[52] U.S. Cl. ..................................... 536/10; 424/180; 536/17
[58] Field of Search ................... 260/210 AB, 210 K; 536/10, 17

[56] References Cited

U.S. PATENT DOCUMENTS

| 3,753,973 | 8/1973 | Umezawa et al. | 260/210 K |
| 3,828,021 | 8/1974 | Beattie et al. | 260/210 AB |
| 3,929,761 | 12/1975 | Umezawa et al. | 260/210 K |
| 3,959,255 | 5/1976 | Chazan et al. | 260/210 K |

FOREIGN PATENT DOCUMENTS

| 8,415 | 4/1965 | Japan | 260/210 K |

Primary Examiner—Johnnie R. Brown
Attorney, Agent, or Firm—Richard R. Lloyd

[57] ABSTRACT

There are disclosed two new antibiotics, 6"-deoxykanamycin B and 6"-deoxytobramycin. These compounds are highly active, broad spectrum antibiotics.

4 Claims, No Drawings

6''-DEOXYKANAMYCIN B AND 6''-DEOXYTOBRAMYCIN

CROSS-REFERENCE TO RELATED APPLICATION

This application is a continuatin-in-part application of co-pending application Ser. No. 523,292 filed November 13, 1974, now abandoned.

BACKGROUND OF THE INVENTION

1. Field of the Invention

This invention relates to two novel semi-synthetic derivatives of Kanamycin B, i.e., 6''-deoxykanamycin B and 6''-deoxytobramycin. These compounds are prepared by dehydroxylation of the 6''- and 3',6''-positions of Kanamycin B.

2. Description of the Prior Art

Kanamycin B is a known antibiotic in Merck Index, 8th Edition, pp. 597–598. Kanamycin B is a compound having the formula

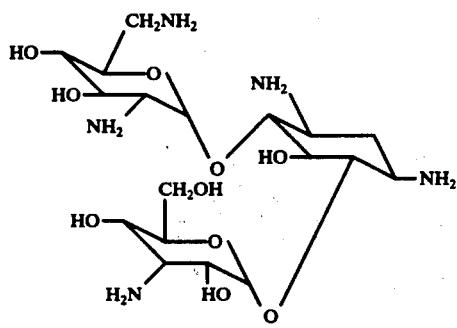

Tobramycin is also a known antibiotic which chemically is known as 3'-deoxykanamycin B. This compound is described by K. F. Koch and J. A. Rhoades in *Antimicrobial Agents And Chemotherapy*, pages 309–313 (1970) as having the formula

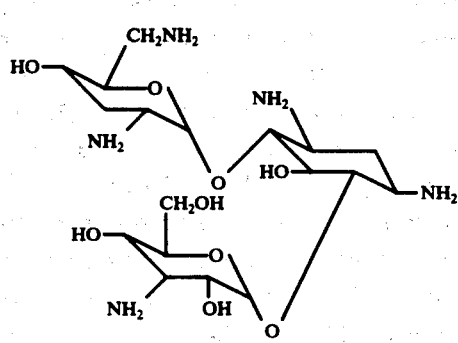

SUMMARY OF THE INVENTION

The compounds having the formula

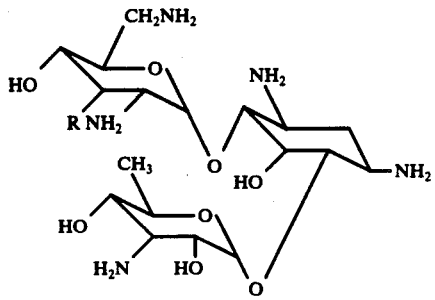

in which R is hydrogen or OH or the nontoxic pharmaceutically acceptable acid addition salt thereof are valuable antibacterial agents.

This invention relates to semi-synthetic derivatives of kanamycin B, said compounds being known as 6''-deoxykanamycin B and 6''-deoxytobramycin and having the formula

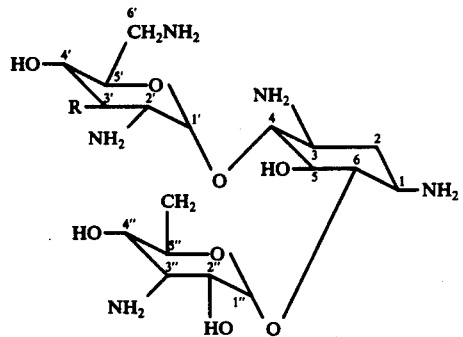

wherein R is hydrogen or OH; or a nontoxic pharmaceutically acceptable acid addition salt thereof.

For the purpose of this disclosure, the term "nontoxic pharmaceutically acceptable acid addition salt" shall mean a mono-, di-, tri-, tetra- or pentasalt by the interaction of 1 molecule of 6''-deoxykanamycin B or 6''-deoxytobramycin with 1–5 moles of a nontoxic, pharmaceutically acceptable acid. Included among these acids are acetic, hydrochloric, sulfuric, maleic, phosphoric, nitric, hydrobromic, ascorbic, malic and citric acid, and those other acids commonly used to make salts of amine containing pharmaceuticals.

The compounds of the present invention are prepared by the following diagrammatic scheme I:

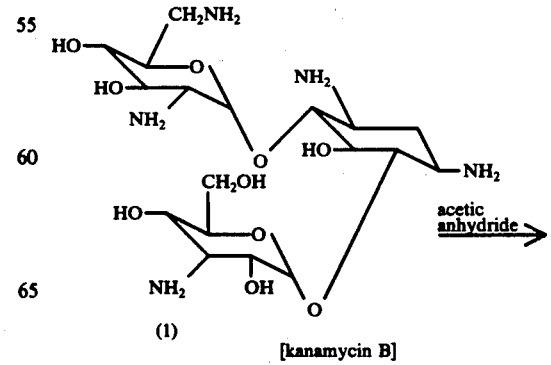

-continued

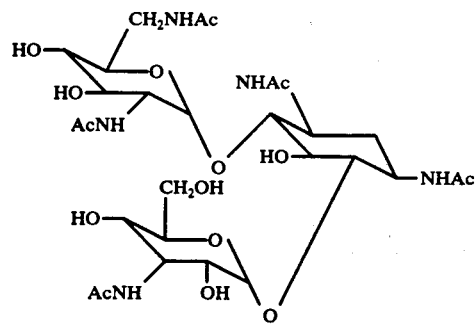

(2) Compound 2 $\xrightarrow{\text{p-toluenesulfonyl chloride}}$

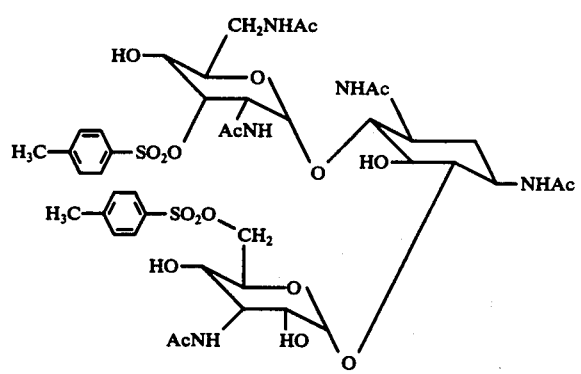

(3) Compound 3 $\xrightarrow{\text{sodium iodide}}$

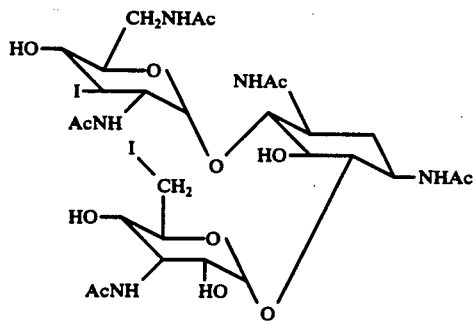

(4) Compound 4 $\xrightarrow{H_2/Ni}$

-continued

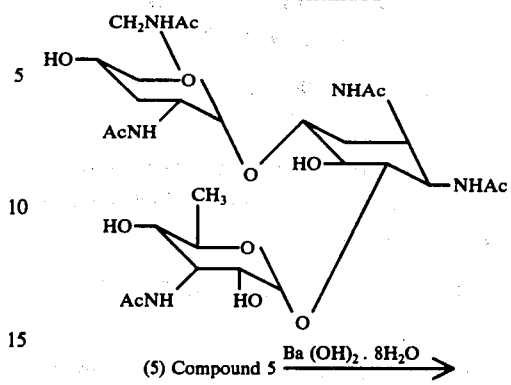

(5) Compound 5 $\xrightarrow{Ba(OH)_2 \cdot 8H_2O}$

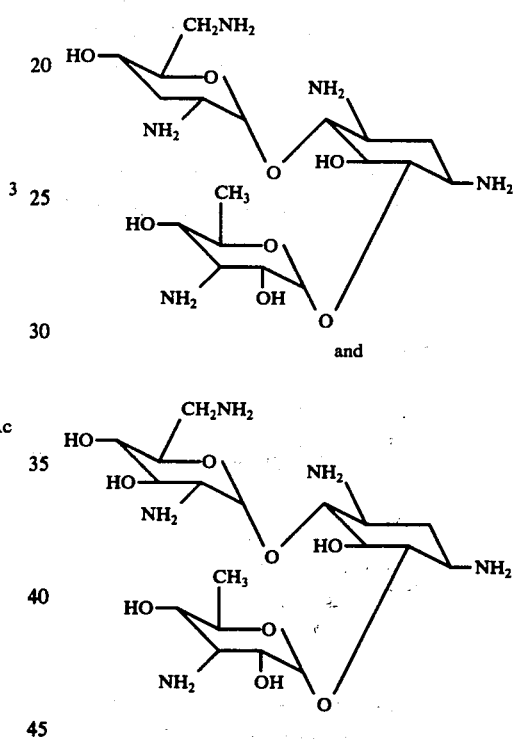

It will be noted that step 5 in the diagrammatic scheme I shows the production of 6"-deoxykanamycin B as well as 6"-deoxytobramycin. The exact mechanism by which 6"-kanamycin B is obtained is not known since one would expect from the preceding steps to obtain only 6"-deoxytobramycin. However, it is hypothesized that in step 2, some 6"-monotosylate of penta-N-acetylkanamycin B may be obtained, in which case, some 6"-iodopenta-N-acetylkanamycin B would be obtained in step 3 and, in step 4, some penta-N-acetyl-6"-deoxykanamycin B would be obtained. However, the analytical data does not confirm the presence of such derivatives in these steps.

The exclusive production of 6"-deoxytobramycin from tobramycin is illustrated in Scheme II.

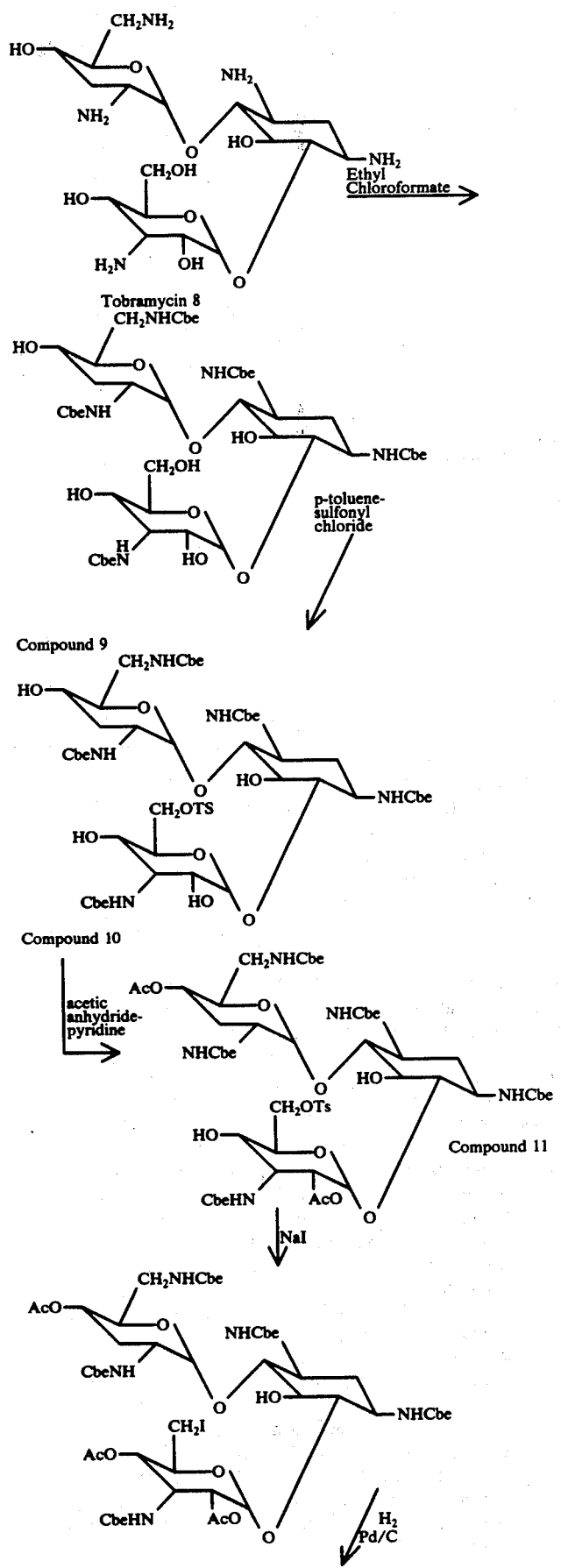

Compound 12

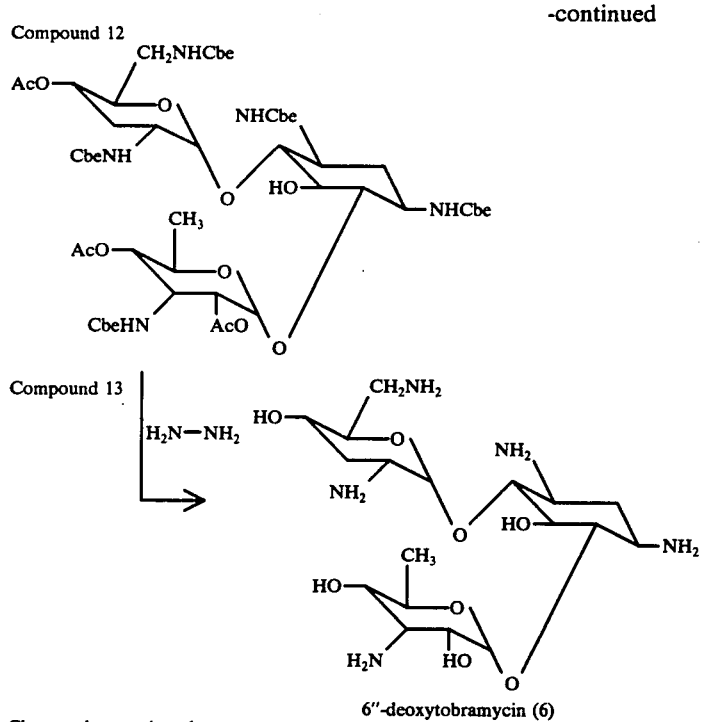

Compound 13

6"-deoxytobramycin (6)

Cbe = ethoxycarbonyl
Ac = acetate
OTS = Tosylate

The objective of the present invention have been achieved, by the provision according to the present invention of the process for the preparation of 6"-deoxytobramycin and 6"-deoxykanamycin B; or a non-toxic pharmaceutically acceptable acid addition salt thereof; which process comprises the following consecutive steps:

A. Kanamycin B or tobramycin is treated with a large molar excess of an acetylating agent, e.g., acetic anhydride or ethyl chloroformate in a lower alkanol or acetone or with acetyl chloride in conjunction with a base to take up free HCl, such as triethylamine or pyridine. By "lower alkanol" is meant an alkanol having up to 4 carbon atoms, e.g., methanol, ethanol, N-propyl alcohol, isopropyl alcohol, N-butyl alcohol, sec-butyl alcohol, iso-butyl alcohol and t-butyl alcohol. Preferably, at least 5.1 moles of acetylating agent are used per mole of kanamycin B and the reaction is conducted at a temperature below 25° C, and, more preferably, at about room temperature. The product obtained by the treatment of kanamycin B with the acetylating agent is penta-N-acylated kanamycin B (2) or tobramycin (9).

B. Penta-N-acylated kanamycin (2) or tobramycin (9) is treated with p-toluenesulfonyl chloride in the presence of a tertiary amine such as pyridine, triethylamine or dimethylaniline. Preferably, at least 2.0 moles of p-toluenesulfonyl chloride per mole of penta-N-acylated aminoglycoside are employed and the reaction is conducted at a temperature below 25° C. and, more preferably, at about room temperature to produce compound (3) or (10).

C. Optionally, when desired treating the 6"-sulfonated-penta-N-acylated aminoglycoside with acetic anhydride in the presence of a base to produce 4', 2", 4"-tri-O-acetyl-penta-N-acyl-6"-O-p-toluene-sulfonyl-tobramycin (11) or 4', 5', 2", 4"-tetra-O-acetyl-penta-N-acyl-6"-O-toluene-sulfonylkanamycin B (11²).

D. The tosylate derivative product (11) or (11²) obtained the step (C) or the products as obtained in step B are reacted with a halide selected from the group consisting of sodium iodide, lithium iodide, sodium bromide or lithium bromide in an appropriate solvent system. The solvent may be a compound selected from the group consisting of N,N-dimethylformamide, or a ketone having the formula

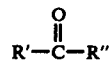

wherein R' and R" are alike or different and each is an alkyl group containing up to 6 carbon atoms. Examples of such ketones include acetone, methyl isobutyl ketone and methyl ethyl ketone. An alternative solvent system is hexamethylphosphortriamide in an aromatic hydrocarbon selected from the group consisting of toluene, benzene, xylene or mixtures thereof, at reflux temperature. About 1.1 mole of hexamethylphosphortriamide should be used in this system per mole of sodium iodide, lithium iodide, sodium bromide or lithium bromide. Preferably, at least 6 moles of halide per mole of tosylate derivative are used and the reaction is conducted at a temperature above 80° C., and, more preferably, at a temperature of from 100° to 125° C. The products obtained are 4', 2", 4"-Tri-O-acetyl-6"-iodo (or bromo)-penta-N-acyl-tobramycin (compound 12) or 4', 5', 2", 4"-tetra-O-acetyl-6"-iodo (or bromo)-penta-N-acylkanamycin B (compound 12²) or the product compound 4.

E. An aqueous solution of the product obtained in step D is hydrogenated in the presence of a known hydrogenation catalyst, e.g. Raney nickel, palladium, platinum, rhodium or ruthenium. The hydrogenation reaction is preferably conducted at about room temperature.

F. An aqueous solution of the product obtained in step D is heated in the presence of a strong base and water; e.g., sodium hydroxide, hydrazine, lithium hydroxide, potassium hydroxide, or barium hydroxide, to hydrolyze the N-actyl and O-acyl groups to yield 6''-deoxykanamycin B or 6''-deoxytobramycin.

Compound 6, 6''-deoxytobramycin, possesses excellent antibacterial activity as illustrated in Table I against a variety of gram-positive and gram-negative bacteria as determined by the two-fold agar dilution method.

pended in 800 ml. of fresh methanol and the suspension was stirred for 1 hour. The solids were collected by filtration and were then stirred with 800 ml. of methylene chloride for 1.5 hours. The product was then collected by filtration, rinsed with methylene chloride and thoroughly dried to give 44.4 g. (77.4% yield) of 2 in the form of a crystalline solid having a melting point of 340°-343° C.

Anal. Calcd. for $C_{28}H_{47}N_5O_{15}$: C, 48.87; H, 6.84; N, 10.09. Found: (Corrected for 1.37% $H_2O$ found): C, 48.62, H, 6.83; N, 10.13.

The infrared and NMR spectra were consistent with the structure 2.

TABLE I

| | | | Run 1 | | Run 2 | |
|---|---|---|---|---|---|---|
| | MIC (mcg/ml) | | 1 CMPD | 2 TOB | 1 CMPD | 2 TOB |
| Ec-1 | E. coli NIHJ | | 0.8 | 0.8 | 0.8 | 0.8 |
| Ec-2 | E. coli P01495 | CP.TC-R | 0.8 | 1.6 | 0.8 | 0.8 |
| Ec-5 | E. coli ML1630 | NPT-1 | 1.6 | 1.6 | 0.8 | 0.8 |
| Ec-9 | E. coli NR79/W677 | KAT | 1.6 | 1.6 | 0.8 | 0.8 |
| Ec-10 | E. coli JR35/C600 | NPT-1 | 0.8 | 1.6 | 0.8 | 1.6 |
| Ec-49 | E. coli A20107 | NPT-2 | 1.6 | 1.6 | 0.8 | 1.6 |
| Ec-53 | E. coli JR66/W677 | NPT-2, GAS | 25 | 25 | 25 | 25 |
| Ec-55 | E. coli R5 | KAT | 0.4 | 0.8 | 0.4 | 0.8 |
| Ec-62 | E. coli JR88 | CAT-1 | 3.1 | 1.6 | 3.1 | 1.6 |
| Ec-72 | E. coli A20732 | GAS | 50 | 50 | 25 | 1.6 |
| Kp-1 | K. pneumoniae D11 | | 0.2 | 0.4 | 0.4 | 0.8 |
| Kp-8 | K. pneumoniae 22-3038 | NPT-2, GAS | 25 | 25 | 25 | 25 |
| El-2 | E. cloacae A20364 | NPT-1 | 1.6 | 50(?) | 1.6 | 1.6 |
| El-12 | E. cloacae A21006 | NPT-2 | 1.6 | 1.6 | 1.6 | 1.6 |
| Pv-1 | P. vulgaris A9436 | | 0.2 | 0.4 | 0.2 | 0.4 |
| Pm-1 | P. mirabilis A9554 | CL-R | 0.8 | 0.8 | 0.8 | 0.8 |
| Ps-2 | P. stuartii A20894 | GAT-2 | 25 | 12.5 | 25 | 12.5 |
| Pa-3 | P. aeruginosa A9930 | | 0.4 | 0.4 | 0.4 | 0.8 |
| Pa-12 | P. aeruginosa A20653 | NPT-1,2 | 6.3 | 6.3 | 3.1 | 3.1 |
| Pa-16 | P. aeruginosa #130 | GAT-1, NPT | 6.3 | 3.1 | 6.3 | 3.1 |
| Pa-21 | P. aeruginosa A20601 | GAT-1 | 3.1 | 3.1 | 3.1 | 1.6 |
| Pa-24 | P. aeruginosa A20896 | GAT-3 | >100 | >100 | >100 | >100 |
| Pa-27 | P. aeruginosa GN-315 | KAT | >100 | >100 | >100 | >100 |
| Pa-45 | P. aeruginosa GN-4925 | | 100 | 100 | 100 | 50 |
| Px-10 | Pseudomonas sp. A20621 | KAT, NPT-1,2 | 50 | 25 | 50 | 25 |
| Sm-1 | S. marcescens A20019 | | 6.3 | 6.3 | 6.3 | 12.5 |
| Sm-16 | S. marcescens A21247 | NPT-1, GAS | 100 | 50 | 50 | 50 |
| Sa-2 | S. aureus Smith | | 0.2 | 0.4 | 0.1 | 0.2 |
| Sa-4 | S. aureus D133 | SH, Sth-R | 1.6 | 1.6 | 1.6 | 1.6 |
| Sa-9 | S. aureus D137 | PC, TC, EM-R | 3.1 | 3.1 | 3.1 | 3.1 |
| Sa-10 | S. aureus A20239 | NPT-1,2 | 0.8 | 1.6 | 0.8 | 1.6 |
| Bs-1 | B. subtilis PCT-219 | | <0.05 | 0.2 | <0.05 | <0.05 |

1 is compound 6.
2 is tobramycin

The compounds of this invention are valuable as antibacterial agents, nutritional supplements in animal feeds, therapeutic agents in poultry and animals including man, and are especially valuable in the treatment of infectious diseases caused by Gram-negative bacteria. They are effective in the treatment of systemic bacterial infections when administered parenterally in the dosage range of about 250 mg. to about 3000 mg. per day in divided doses three or four times a day. Generally, the compounds are effective when administered at a dosage of about 5.0 to 7.5 mg./kg. of body weight every 12 hours.

EXAMPLES

Example 1

Penta-N-acetylkanamycin B (2)

To a stirred suspension of 40.0 g. (0.0827 mole) of kanamycin B in 800 ml. of methanol was added dropwise 117.2 ml (1.24 moles) of acetic anhydride. Before all of the acetic anhydride was added, a clear solution was obtained but almost immediately thereafter a precipitate began to form. Stirring was continued for 16 hours after completing the addition of acetic anhydride. During this time, the reaction mixture solidified and several hundred ml. of methanol were added in order to obtain a filterable mixture. The damp solids were sus-

Example 2

Penta-N-acetylkanamycin B-3', 6''-ditosylate (3)

A mixture of 1.000 g. of penta-N-acetylkanamycin B (1.442 mmole) and 1.645 g. of p-toluenesulfonylchloride (8.649 mmole) in 10 ml. of anhydrous pyridine was stirred at room temperature for 23¼ hrs. The reactants dissolved slowly and were completely dissolved in 5 hours. After 5 hours, the solution was orange in color and the color did not change during the remainder of the reaction. The reaction mixture was poured into 200 ml. of methylene chloride and the resultant precipitated creamy-white product was dried thoroughly. It was then suspended in 30 ml. of methylene chloride and heated at reflux for 2 minutes. The insoluble solid was recovered from the hot solvent by filtration and thoroughly dried over $P_2O_5$ to give 1.043 g. (72.2% yield) of 3. The infrared spectrum showed typical tosylate bands at 1180 and 1220 cm.$^{-1}$. A sample of the product was subjected to liquid chromatography by injecting 35 microliters of a suspension of 1 ml. of the product per ml. of a solution consisting of 30% water and 70% methanol onto a tandem group of four ⅛ in. × 2 ft. columns. The columns were packed with $C_{18}$/CORASIL I, a monomolecular layer of octadecyltrichloro-silane chemically bonded to a porous silica layer on a solid glass bead core. It was found that the product consisted of a very minor component with a retention time of 16½ minutes and a major component with a retention time of 19¾ minutes.

Anal. Calcd. for $C_{42}H_{59}N_5O_{19}S_2$: C, 50.34; H, 5.93; N, 6.99; S, 6.40. Found (corrected for 2.66% moisture found): C, 48.67; H, 5.64; N, 6.83; S, 5.87.

Example 3

Penta-N-acetyl-3',6"-diiodokanamycin B (4)

A mixture of 834 mg. of the product obtained in Example 2 (0.832 mmole) which had been dried in vacuo over $P_2O_5$ at room temperature, and 1.998 g. of sodium iodide (13.3 mmole) which had been air dried in an oven at 110° C. for 20 hours, in 1.5 ml. of N,N-dimethylformamide was placed in a 60 ml. heavy-walled glass vial which was purged with $N_2$ and heated at 100° C for 23 hours. The vial was then opened, cooled and filled with ether. After several hours, the ether was decanted and the residue was heated on a steam bath until a thick syrup was formed. The vial was then filled with dioxane, heated up to 90° C. and the insoluble solids, which included the desired product, were recovered by filtration, rinsed with ether and dried over $P_2O_5$ in vacuo. The recovered solids were de-salted by dispersing them in 15 ml. of water and then removing the water insoluble solids by filtration over a bed odf diatomaceous earth. The filtrate was passed over an 800 ml. column of Sephadex G10, a cross-linked dextran having a molecular weight retention of up to about 700. The column was pumped at 1 ml./min. and 27 ml. fractions were collected. The product was determined to be in tubes 11-21. The components of these tubes were combined, reduced to a volume of 20 ml. by evaporation at 50° C. and the product, 504 mg. of 4 (66.3% yield), was recovered therefrom by lyophyllization. This product was used directly in the next example further purification.

Example 4

Penta-N-acetyl-6"-deoxytobramycin (5)

An aqueous solution of 388 mg. of the product obtained in Example 3 (0.425 mmole) in 60 ml. of water was hydrogenated for 21 hours in the presence of about 4 gm. of Raney nickel catalyst at room temperature and at a hydrogen pressure of 44 psi. The catalyst was then filtered off and washed thoroughly with water. The combined filtrates were evaporated to dryness at 50° C. and dried over $P_2O_5$ in vacuo to give 180 mg. (63.1% yield) of 5.

Example 5

6"-Deoxytobramycin (6) and 6"-deoxykanamycin B (7)

A mixture of 180 mg. of the product obtained in Example 4 (0.272 mmole), 2.55 g. of $Ba(OH)_2.8H_2O$ (8.08 mmole) and 10.2 ml. of water was heated at reflux for 17 hours. The reaction mixture was then diluted to 35 ml. by the addition of water and solid carbon dioxide was added until the pH fell to 7.0. The resultant $BaCO_3$ was removed by filtration over fine filter paper and washed with a few ml. of water. The combined filtrates were flashed down to 10 ml. and then lyophyllized. The crude product weighed 170 mg. The product was dissolved in 2.00 ml. of water for analysis by thin layer chromatography on a column of silica gel S110 using the solvent system $H_2O:CH_3OH$: conc. $NH_4OH:CHCl_3$ (1:4:2:1). The analysis showed that kanamycin B had an $R_f$ = 0.52, while the two major ninhydrin-positive components of the product mixture had $R_f$ = 0.47 and $R_f$ = 0.61. When a duplicate plate was overlaid with an agar plate seeded with Bacillus subtilis at a pH of 8 and incubated overnight at 37° C., large zones of inhibition were found at $R_f$ = 0.47 and $R_f$ = 0.61. A 0.100 ml. aliquot of the 2.00 ml. solution of the crude product was diluted to 5.00 ml. with 0.1 N phosphate buffer having a pH of 8.0 and submitted for a differential bioassay for tobramycin-like and kanamycin B-like activities. The yield of 6"-deoxytobramycin is determined from the bioassay data to be about 7.1% and the yield of 6"-deoxykanamycin B is calculated from the bioassay data to be about 1.5%.

Example 6

Penta-N-ethoxycarbonyltobramycin (9)

To a solution of tobramycin sulfate [8, 4.4g] (4.4 g) and potassium carbonate (7.0 g) in water (100 ml) were added acetone (100 ml) and ethyl chloroformate (5.0 g) successively at 5° C. with stirring. The mixture was stirred for 1.5 hrs. at 5°–10° C. and for additional 3 hrs. at room temperature. Insoluble material was filtered and washed with acetone. The combined filtrate and washings were concentrated in vacuo to ca. 100 ml to separate precipitate, which was collected by filtration, washed with water, and dried at 65° for 2 hrs. to give 4.0 g. of 9 (78%).

IR: $\nu_{C=O}$ 1690 cm$^{-1}$. NMR (DMSO-d$_6$): δ(ppm), 1.17 (15H, t, J=7 Hz, C$\underline{H}_3$CH$_2$O), 3.94 (10H, q, J=7 Hz, CH$_3$C$\underline{H}_2$O).

Example 7

Penta-N-ethoxycarbonyl-6"-O-p-toluenesulfonyltobramycin (10).

To a cold solution (−30° C) of 9 (4.14 g., 5 m moles) in dry pyridine was added p-toluenesulfonyl chloride (1.24 g., 6.5 m moles) with shaking. The mixture was kept at the same temperature for 65 hrs. and then water (5 ml) was added to the reaction mixture at room temperature. After 2 hrs., the solvent was evaporated in vacuo. The residual syrup was poured into cold water and extracted with chloroform (X3). The combined extracts were washed with a saturated solution of sodium hydrogen carbonate and the chloroform was evaporated. The residue was chromatographed on a short column of silica gel (300 g) and eluted with chloroform-methanol (10:1). The eluate was fractionated (50 ml). Fractions No. 18–39 were collected and evaporated to give 1.88 g of 10. Fractions No. 12–17 were combined and rechromatographed (silica gel 100 g, chloroform-methanol = 15 : 1) to afford additional 0.73 g of 10. Total yield, 2.61 g (53%). IR (KBr): 1690, 1170 cm$^{-1}$. NMR (DMSO-d$_6$): δ(ppm) 1.0–1.5 (15 H, m, CH$_2$C$\underline{H}_3$), 2.44 (3H, s, PhC$\underline{H}_3$), 4.91 (2H, m, H-1' and H-1"), 7.25 (2H, d, J=9 Hz, Ph) and 7.63 (2H, d, J=9 Hz).

A positional isomer of 10 was obtained from fractions No. 43–71 (0.57 g., 12%), and 9 was also recovered from fractions eluted with chloroform-methanol (5:1) (0.98 g, 10%). A ditosyl derivative was obtained from eluates in the rechromatography (0.52 g, 10%).

Example 8

4', 2", 4"-Tri-O-acetyl-penta-N-ethoxycarbonyl-6"-O-p-toluenesulfonyltobramycin (11).

A solution of 10 (1.00 g) in pyridine-acetic anhydride (8:1, 45 ml) was kept at room temperature for 20 hrs. To the reaction mixture was added water (10 ml) with cooling and the solution was evaporated after standing at room temperature for 1 hr. The residue was dissolved into toluene and evaporated again to remove the remaining pyridine, and recrystallized from ethyl acetate-n-hexane to give 972 mg of the 6''-O-tosylate (11) (86%); mp. 242°-4° C (dec.). IR (KBr): 1740, 1690, 1230, 1170 cm$^{-1}$. NMR (CDCl$_3$): δ(ppm) 1.0–1.4 (15H, m, CH$_2$C$\underline{H}_3$), 1.88, 2.02, 2.05 (each 3H, s, COC$\underline{H}_3$), 2.45 (3H, s, PhC$\underline{H}_3$), 7.25 and 7.65 (each 2H, d, J=9 Hz, Ph).

Anal. Calc'd. for C$_{46}$H$_{69}$N$_5$O$_{24}$S: C, 49.86; H, 6.28; N, 6.32; S, 2.89%. Found: C, 49.87; H, 6.34; N, 6.19; S, 3.10%.

Example 9

4', 2'', 4'''-Tri-O-acetyl-6''-iodo-penta-N-ethoxycarbonyl-tobramycin (12)

A mixture of 11 (837 mg) and sodium iodide (10 g) in acetone was kept at 100° C. for 2 hrs. in a sealed tube. The organic layer, which was separated from the tube by decantation, was evaporated, and the residue was dissolved in chloroform. The precipitate in the tube was dissolved in water and extracted with chloroform (X3). The chloroform solutions were combined, washed with water, and evaporated to yield 860 mg of the 6''-iodo derivative (12), which showed positive Beilstein test. NMR (CDCl$_3$): δ(ppm), 1.24 (15H, br-t, J=7 Hz, CH$_2$C$\underline{H}_3$), 2.03, 2.06 and 2.12 (each 3H, s, COC$\underline{H}_3$), 4.06 (10H, br-q, J=7 Hz, OC$\underline{H}_2$CH$_3$). No aromatic proton and no PhC$\underline{H}_3$ singlet appeared, which indicated the absence of a tolyl group.

Example 10

4', 2'', 4'''-Tri-O-acetyl-6''-deoxy-penta-N-ethoxycarbonyltobramycin (13).

A mixture of the crude 12 (860 mg), 10% Pd-C (860 mg), dioxane (20 ml), and a saturated aqueous solution of sodium hydrogen carbonate (10 ml) was shaken for 20 hrs. with hydrogen under atmospheric pressure. The reaction mixture was filtered and washed with dioxane. The filtrate was combined with the washings and evaporated. The chloroform solution of the residue was washed with water (X3), a dilute sodium thiosulfate solution, and saturated sodium hydrogen carbonate solution successively, and evaporated to dryness. The residue (880 mg) was crystallized from methanol to afford 650 mg of the 6''-deoxy derivative (13) (81% from 11); mp >300° C. IR (KBr): 1730, 1690, 1230 cm$^{-1}$. NMR (CDCl$_3$): δ(ppm), 1.0–1.4 (18H, m, C$\underline{H}_3$), 2.08 (6H, s, COC$\underline{H}_3$), 2.12 (3H, s, COC$\underline{H}_3$), 4.10 (10H, br-q, J=7 Hz, OC$\underline{H}_2$CH$_3$).

Anal. Calcd. for C$_{39}$H$_{63}$N$_5$O$_{21}$: C, 49.94; H, 6.77; N, 7.47%. Found: C, 49.84; H, 6.79; N, 7.36%.

Example 11

6''-Deoxytobramycin (BB-K228) (6).

A suspension of crude 13 (764 mg) and 80% hydrazine hydrate was reacted at 140°-150° C. for 3 days in a sealed tube. The reaction mixture was dissolved in water and evaporated to remove thoroughly the remaining hydrazine. An aqueous solution of the residue was neutralized with 1N HCl to pH 7 and chromatographed on a short column of Amberlite CG-50 (NH$_4$, 100 ml), which was washed with 500 ml. of water and then eluted with 0.2 N NH$_4$OH. On monitoring with TLC (S-110* , ninhydrin), fractions showing Rf 0.59 were collected and evaporated to give 254 mg of the crude product, which was repeated twice chromatography on a short column of Amberlite CG-50 (NH$_4$, 8 ml) using 0.2 N NH$_4$OH as an eluant which was prepared with CO$_2$-free water. The fractions showing strong ninhydrine positive reaction were collected and evaporated to give 212 mg. of BB-K228 (VI) (68% based on III). IR (KBr): 3400 (br.) 1600, 1040 cm$^{-1}$. NMR (D$_2$O): δ(ppm), 1,21 (3H, d, J=6 Hz, CHC$\underline{H}_3$), 1.4–2.4 (4H, m, CH$_2$), 4.93 (1H, d, J=4 Hz), 5.10 (1H, d, J=3.5 Hz).

* S-110: silica gel, CHCl$_3$-MeOH-concNH$_4$OH-H$_2$O (1:4:2:1).

Anal. Calc'd. for C$_{18}$H$_{37}$N$_4$O$_8$.H$_2$O: C, 46.04; H, 8.37; N, 14.91%. Found: C, 46.44; H, 8.97; N, 15.03%

Amberlite CG 50 is the trade name for the chromatographic grade of a weakly acidic cationic exchange resin of a carboxylic-polymethacrylic type.

We claim:

1. A compound having the formula

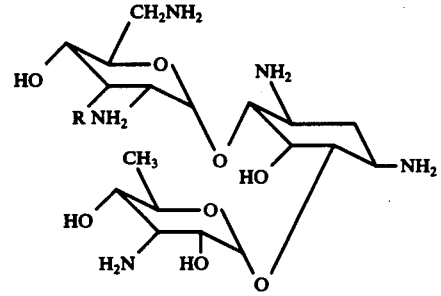

in which R is hydrogen or OH; or a nontoxic pharmaceutically acceptable acid addition salt thereof, 2. The compound of claim 1 wherein R is hydrogen 3. The compound of claim 1 wherein R is OH.

4. The mono- or disulfate salt of the compound of claim 2.

* * * * *